United States Patent
Carrel

(10) Patent No.: US 10,569,029 B2
(45) Date of Patent: Feb. 25, 2020

(54) SAFETY DEVICE FOR PREVENTING NEEDLE STICK INJURY WITH A NEEDLE OF A MEDICAL DEVICE AND MEDICAL DEVICE

(71) Applicant: Becton Dickinson France, Le Pont de Claix (FR)

(72) Inventor: Franck Carrel, Saint Jean de Vaulx (FR)

(73) Assignee: Becton Dickinson France, Le Pont de Claix (FR)

( * ) Notice: Subject to any disclaimer, the term of this patent is extended or adjusted under 35 U.S.C. 154(b) by 106 days.

(21) Appl. No.: 15/571,958

(22) PCT Filed: Jun. 7, 2016

(86) PCT No.: PCT/EP2016/062875
§ 371 (c)(1),
(2) Date: Nov. 6, 2017

(87) PCT Pub. No.: WO2016/198387
PCT Pub. Date: Dec. 15, 2016

(65) Prior Publication Data
US 2018/0140780 A1  May 24, 2018

(30) Foreign Application Priority Data

Jun. 8, 2015  (EP) .................................... 15305866
Nov. 13, 2015  (EP) .................................... 15306800

(51) Int. Cl.
*A61M 5/32* (2006.01)
*A61M 5/34* (2006.01)

(52) U.S. Cl.
CPC ........ *A61M 5/3202* (2013.01); *A61M 5/3216* (2013.01); *A61M 5/343* (2013.01)

(58) Field of Classification Search
CPC .. A61M 5/3202; A61M 5/3216; A61M 5/343; A61M 2005/325; A61B 2090/0801; A61B 17/3494
See application file for complete search history.

(56) References Cited

U.S. PATENT DOCUMENTS 5,405,332 A    4/1995  Opalek
5,665,075 A    9/1997  Gyure et al.
(Continued)

FOREIGN PATENT DOCUMENTS

EP        0832660 A2    4/1998
WO    2012152207 A1   11/2012
(Continued)

*Primary Examiner* — Brandy S Lee
(74) *Attorney, Agent, or Firm* — The Webb Law Firm

(57) ABSTRACT

The present invention relates to a safety device (100) for preventing needlestick injury with a needle (20), comprising: a protective cap (130) and a shield (120) capable of pivoting from a storage position where it is interlocked with the protective cap (130), a retracted position where it gives access to the needle (20) and a safety position where it covers the needle (20), wherein a cam surface (127) of the shield and an engaging peg (137) of the protective cap are arranged so that, when the safety device (100) is mounted around the tip (14) of a medical device (10), removing the protective cap (130) from the tip (14) by a distal movement displaces the shield (120) from the storage position to the retracted position. Furthermore, the present invention relates to a medical device (10) comprising a tip (14) provided with a needle (20) comprising a needle point (22), wherein the medical device (10) further comprises a safety device (100).

9 Claims, 8 Drawing Sheets

(56) References Cited

U.S. PATENT DOCUMENTS

2003/0078548 A1* 4/2003 Kobayashi .......... A61M 5/3216
 604/263
2010/0049141 A1 2/2010 Gardner
2015/0352291 A1 12/2015 Fournier et al.

FOREIGN PATENT DOCUMENTS

WO 2013029529 A1 3/2013
WO 2014131981 A1 9/2014

* cited by examiner

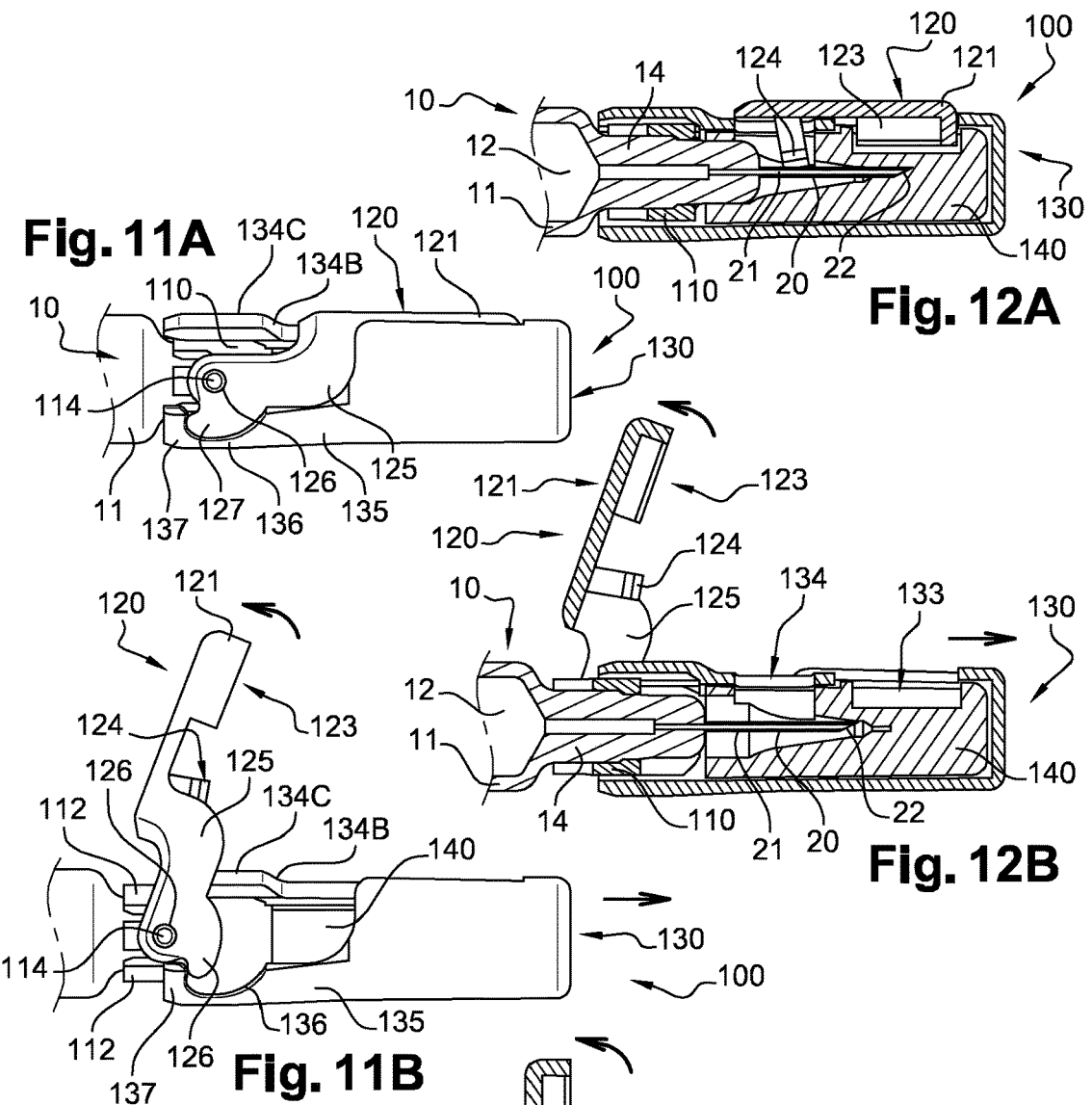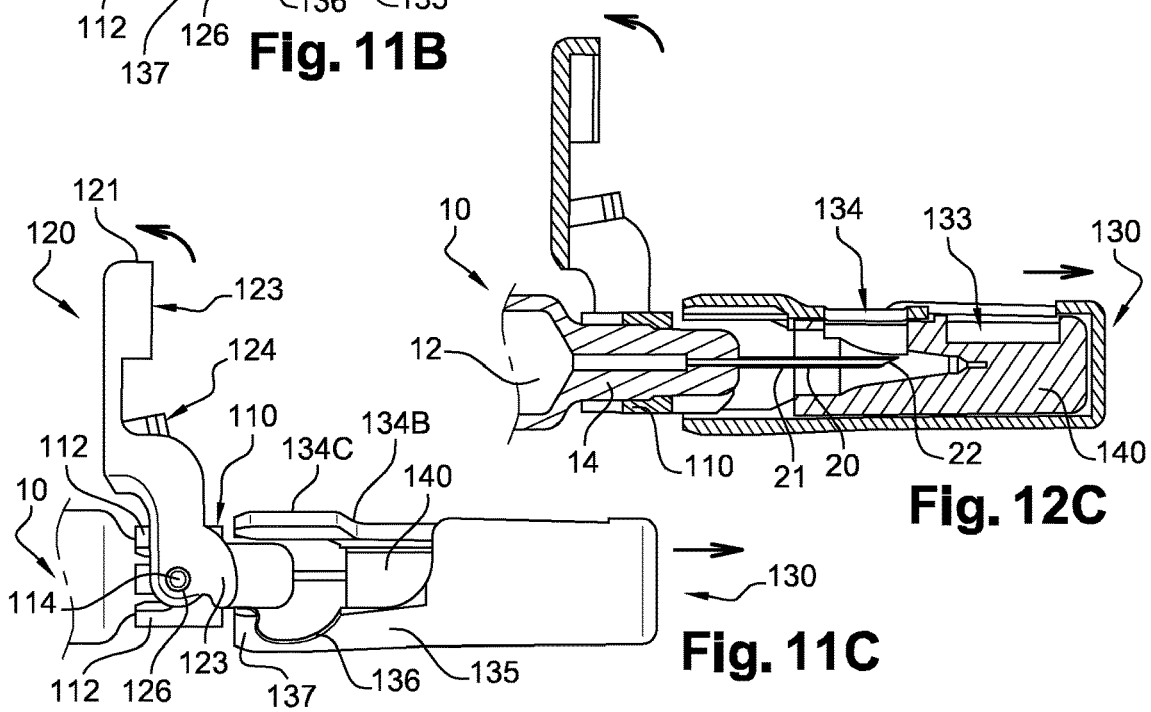

SAFETY DEVICE FOR PREVENTING NEEDLE STICK INJURY WITH A NEEDLE OF A MEDICAL DEVICE AND MEDICAL DEVICE

CROSS-REFERENCE TO RELATED APPLICATIONS

This application is the United States national phase of International Application No. PCT/EP2016/062875 filed Jun. 7, 2016, and claims priority to European Patent Application Nos. 15305866.4 and 15306800.2, filed Jun. 8, 2015 and Nov. 13, 2015, respectively, the disclosures of which are hereby incorporated in their entirety by reference.

BACKGROUND OF THE INVENTION

Field of the Invention

The present disclosure relates to a safety device for preventing needle stick injury with a needle of a medical device. The present disclosure also relates to a medical device including such a safety device.

Description of Related Art

In this application, the distal end of a component or apparatus must be understood as meaning the end furthest from the hand of the user and the proximal end must be understood as meaning the end closest to the hand of the user, with reference to the medical injection device intended to be used with said component or apparatus. As such, in this application, the distal direction must be understood as the direction of injection with reference to the medical device, and the proximal direction is the opposite direction to said direction of injection.

Medical devices provided with sharp pointed needles are of daily practice among the medical community in order to perform injections or to take samples into or from muscles, veins or arteries. They can be injection devices such as syringes, pen-injectors, catheters or blood collection devices. Sharp pointed needles present an inherent risk of needle stick injury for the medical staff and the patients and are thus usually provided with a needle cap covering the needle before use. This cap not only preserves the needle from contamination but also from undesired contacts or punctures that could occur during transport and delivery by the medical staff. Obviously, such a cap needs to be removed immediately before use of the medical device.

However, replacing the needle cap onto the needle after use is strictly prohibited as it is regarded as a major cause of accident and contamination for the medical staff. Indeed, the whole medical device or at least the used needle should be disposed after use in an appropriate needle collector. However, a risk of needle stick injury still exists as the medical staff handles the bare, contaminated needles before disposal.

Safety devices have thus been designed to prevent needle stick injury with the needle of such medical devices after use i.e. between the end of the injection or collection and the proper disposal of the device. Usually, such safety systems are designed to be locked automatically or manually on at least the needle point when the medical act is finished.

Nevertheless, many of these safety systems required a triggering step in order to expose the needle point before use, which slows down the pace of the medical act and decreases the safety level of the medical device. In addition, the majority of such safety systems increase the overall size of the device leading to difficult handling but also to storage concerns particularly for prefilled syringes. Finally, most of these systems do not achieve a complete exposure of the needle point and impede the medical act by preventing direct view and access to the needle point.

Additionally, prefillable syringes are transported in sterile packaging after manufacturing in order to be filled by the pharmaceutical companies with a pharmaceutical product before the final delivery to the medical staff. The sterile packaging is adapted to the length and diameter of the syringe closed with a usual needle cap and may not accept oversized safety devices as currently available.

SUMMARY OF THE INVENTION

Starting from the prior art, it is an object of the present disclosure to provide a safety device able to prevent needle stick injury with the needle of a medical device without requiring a triggering step before use and without impeding the medical act. It is a further object of the present disclosure to provide a safety device of appropriate size that has a diameter no greater than the syringe barrel and a limited length in order to be accommodated in a standard packaging used for prefillable syringes.

Accordingly, a safety device for preventing needle stick injury with a needle of a medical device is given, the needle including a proximal end fixed to a tip of the medical device and a distal end provided with a needle point. The safety device includes a protective cap adapted to be mounted on the tip of a medical device to at least cover the needle point, said protective cap including a proximal extremity provided with an engaging peg, and a shield adapted to be mounted by a pivot link around the tip of the medical device such that it may adopt a storage position where it is interlocked with the protective cap, a retracted position where it gives access to the needle and a safety position where it covers the needle, the shield including a cam surface at its proximal extremity. The cam surface and the engaging peg are located proximally from the pivot link and arranged so that, when the safety device is mounted around the tip of a medical device, removing the protective cap from the tip by a distal movement shifts the shield from the storage position to the retracted position.

The pivotal mounting of the shield as well as the engagement of the engaging peg of the protective cap with the cam surface of the shield allow a passive opening of the shield into the retracted position in order to give a full access to the needle point. In this way, the removal movement of the protective cap from the tip yields to the rotation of the shield from the storage position to the retracted position, the engagement between the engaging peg and the cam surface transforming an axial movement into a rotational movement. No additional triggering step is thus required to use such a medical device provided with such a safety device: the medical act is not slow down and no training is required for the medical staff. The proximal location of the cam surface and the engaging peg as regards as the pivot link allows the shield to reach substantially a right angle with the needle when the shield is in the retracted position. This right angle is particularly valuable so as not to prevent a direct view of the needle by the medical staff and not to hamper the injection. The safety system of the present invention thus brings needle stick prevention to medical staff with no or limited impact on the medical practice, thus optimizing the acceptance of such a safety system by medical professionals.

Furthermore, the interlocking of the protective cap and the shield leads to a compact and small size device, with an external diameter of the safety device no greater than the external diameter of the medical device. This is particularly valuable when the medical device is a prefillable syringe as standard packaging used for devices storage does not accept oversized safety systems. Prefillable syringes may thus be equipped with such a safety system immediately after manufacturing packaged in standard existing packaging and then directly shipped to the pharmaceutical company. In this way, the filling process performed by pharmaceutical companies may not be affected by the presence of the safety device.

In a preferred embodiment, the shield is provided with two cam surfaces and the protective cap is provided with two engaging pegs. Such an embodiment allows a more reliable passive opening of the shield when the protective cap is removed from the tip.

In a further preferred embodiment, the shield is provided with two proximal legs, each leg including a buckle. The safety system further includes a mounting ring adapted to be mounted onto the tip of the medical device and provided with two opposing inserts. The opposite inserts are adapted to be assembled with the buckles of the shield in a pivoting link so as to pivotally mount the shield to the tip when said mounting ring is arranged on the tip. This optional mounting ring is valuable for mounting the safety device on a tip which cannot be manufactured with the opposing inserts such as to form a pivot link with the shield. This is the case for example with glass syringes, as the tip is made by glass forming which is not an appropriate technique to elaborate tiny features such as opposite inserts.

In a preferred embodiment, the shield is further provided with a hook such that, when the safety device is mounted on the tip of a medical device and the shield is in the safety position, said hook is able to irreversibly lock said shield onto the needle. The hook therefore contributes to the safety position of the shield by preventing the shield to move back to the retracted position, thus protecting patients and medical staff from needle stick injury.

In a further preferred embodiment, the protective cap further includes a proximal radial opening positioned and dimensioned to accommodate the hook of the shield when the shield is in the storage position. This proximal radial opening allows for an optimal interlocking between the shield and the protective cap and thus for a small sized safety device showing a size similar to a usual needle cap. This small sized safety device may thus be accommodated into a standard sterile packaging commonly used for prefillable syringes.

In a further preferred embodiment, the shield is further provided with a notch, so that, when the safety device is mounted on the tip of a medical device and the shield is in the safety position, the notch hides the needle point. The notch therefore contributes to the safety position of the shield by masking the needle point, thus preventing any access to it and then protecting patients and medical staff from needle stick injury.

In a further preferred embodiment, the protective cap further includes a distal radial opening positioned and dimensioned to accommodate the notch of the shield when the shield is in the storage position. This distal radial opening allows an optimal interlocking between the shield and the protective cap and thus leads to a small sized safety device adapted to prefillable syringes.

In a further embodiment, a medical device is given, which includes a tip provided with a needle including a proximal end fixed to the tip of the medical device and a distal end provided with a needle point. The medical device further includes a safety device as mentioned above. Such a medical device provides a high level of safety to the medical staff and the patients when the safety device is placed in the safety position after use. Furthermore, as the safety device is passively opened from the storage position to the retracted position by removing the protective cap, no specific medical instructions are required to use it. Besides, as such a medical device presents a similar size as a current existing medical device without a safety device, it may be assembled and stored in a standard packaging before shipping to a pharmaceutical company for future filling with a medical composition. A safe medical device may thus be provided to the medical staff without any change in the filling process of the pharmaceutical company.

BRIEF DESCRIPTION OF THE DRAWINGS

Preferred further embodiments and aspects of the present in disclosure are explained further by the following description of the Figures:

FIGS. 3, 3A and 3B are respectively a top view and a perspective view of a mounting ring according to the present disclosure.

FIGS. 11A-11F are side views of a safety device according to FIGS. 10A-10C provided on the medical device of FIG. 1 at each step of use.

FIGS. 12A-12F are cross-section views of a safety device according to FIGS. 10A-10C provided on the medical device of FIG. 1 at each step of use.

DETAILED DESCRIPTION OF THE DISCLOSURE

Figure 1:
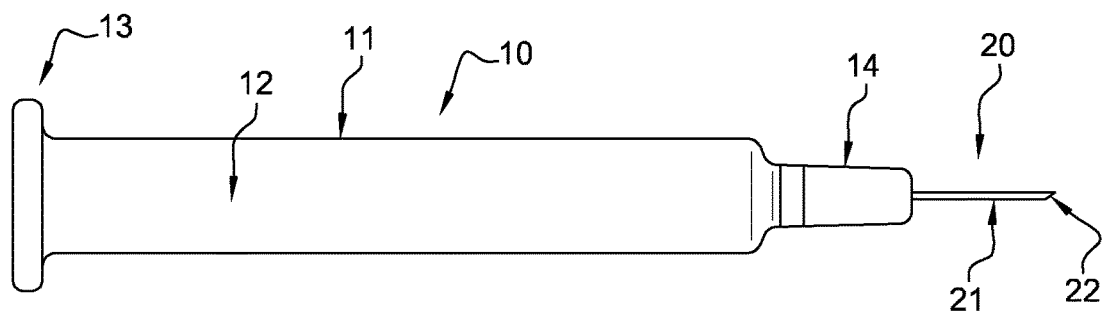
FIG. 1 shows an example of a medical device in the form of a syringe.

FIG. 1 discloses a syringe 10 as an example of a medical device according to the present disclosure. The syringe 10 includes a longitudinal barrel 11 defining a reservoir 12, the longitudinal barrel 11 having an open proximal end defining a flange 13 and a restricted distal end defining a longitudinal tip 14 provided with a needle 20. The syringe 10 may be in glass or in plastic, the following disclosure mainly considering a glass syringe. Other medical devices may be pen-injectors or autoinjectors.

The needle 20 includes a longitudinal tube 21, a proximal open end stacked or glued in the longitudinal tip 14 and a distal open end comprising a needle point 22.

Figure 2:
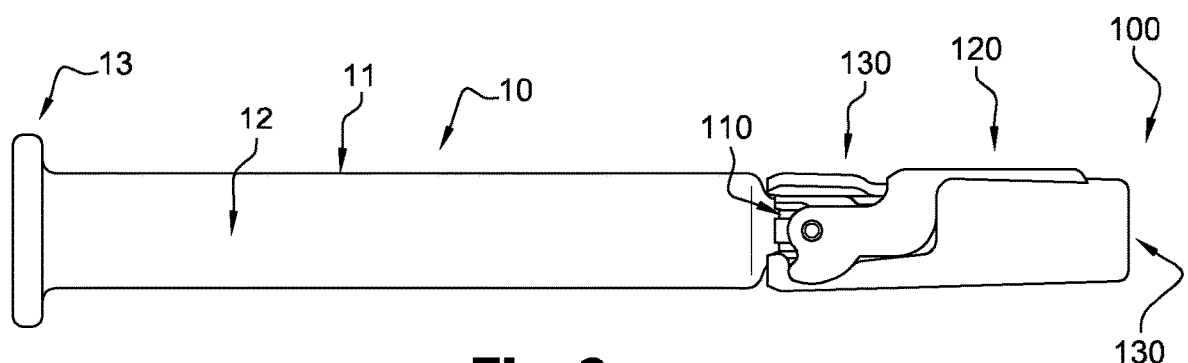
FIG. 2 shows an example of a medical device provided with a safety device according to the present disclosure.

Referring to FIG. 2, the syringe 10 is provided with a safety device 100 including a mounting ring 110, a shield 120 and a sealing cap 130.

Figures 3A, 3B:
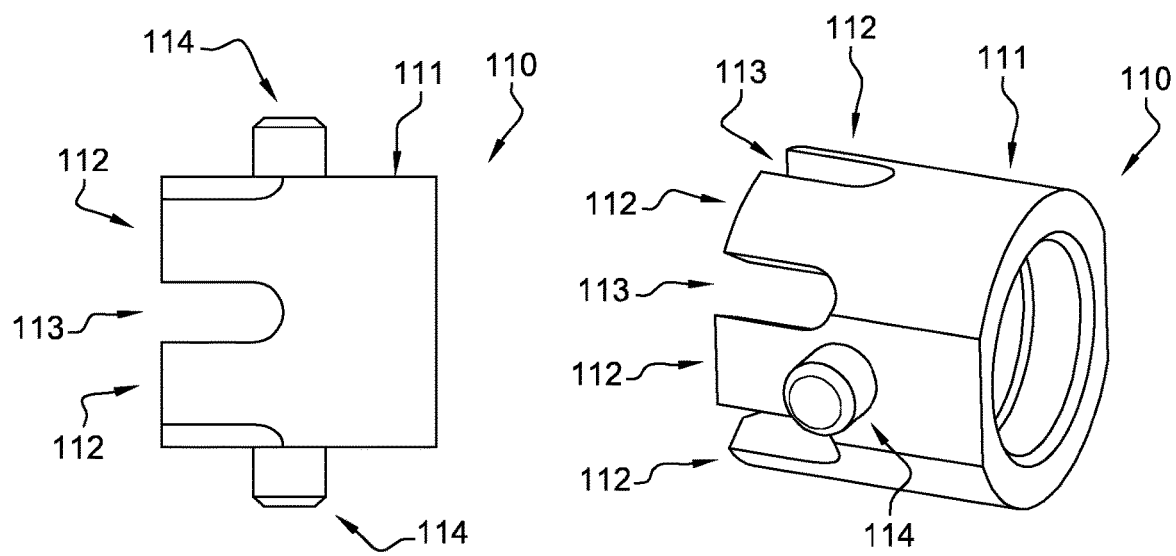

FIGS. 3A and 3B disclose an example of a mounting ring 110. The mounting ring includes a cylindrical body 111 provided with proximal mounting fingers 112 separated by voids 113 and two opposite inserts 114 (only one visible in FIG. 2B).

Figure 4:
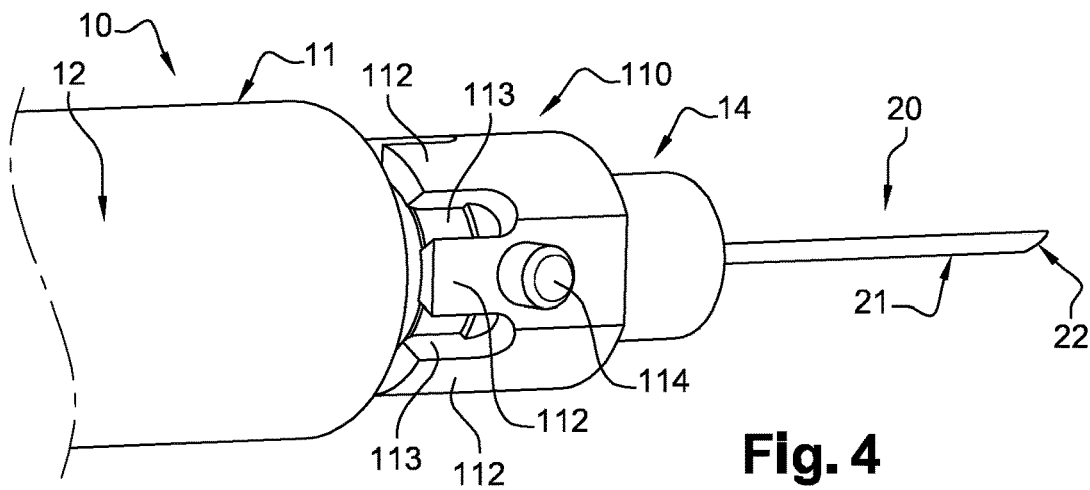
FIG. 4 is an example of a medical device provided with the mounting ring of FIGS. 3A and 3B.

The proximal mounting fingers 113 allow for the arrangement of the mounting ring 110 onto the longitudinal tip 14 of the syringe 10, as visible in FIG. 4. The mounting ring 110 is preferably made of any rigid polymer adapted to medical use, such as high density polyethylene (PE), polypropylene (PP), polycarbonate (PC), acrylonitrile butadiene styrene (ABS), polyoxymethylene (POM), polystyrene (PS), polybutylene terephthalate (PBT), polyamide (PA), and their combinations. The mounting ring 110 may also be made of a medical-grade metal such as steel.

Figure 5A:
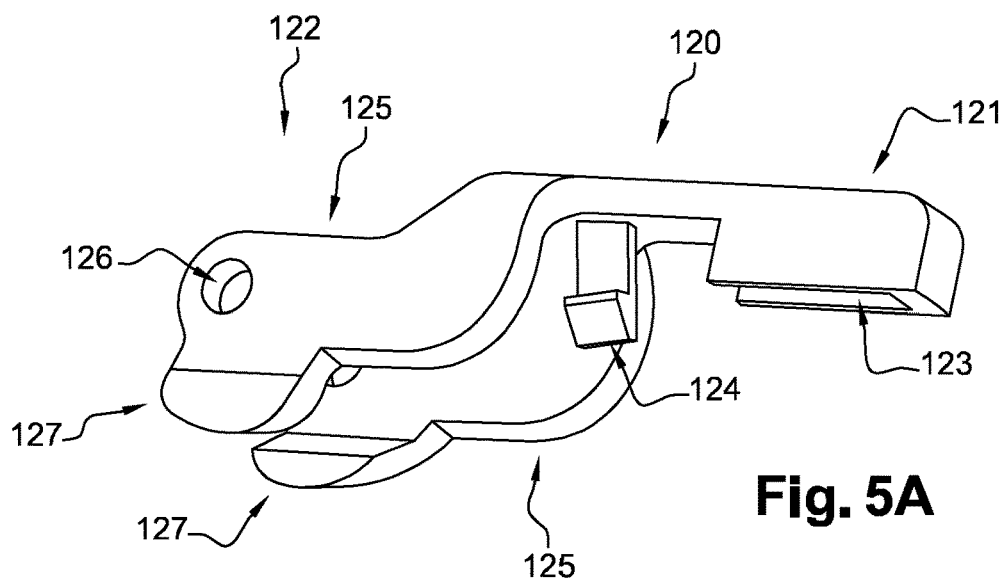
FIGS. 5A and 5B are respectively a perspective view and a top view of a shield according to the present in disclosure.
Figure 5B:
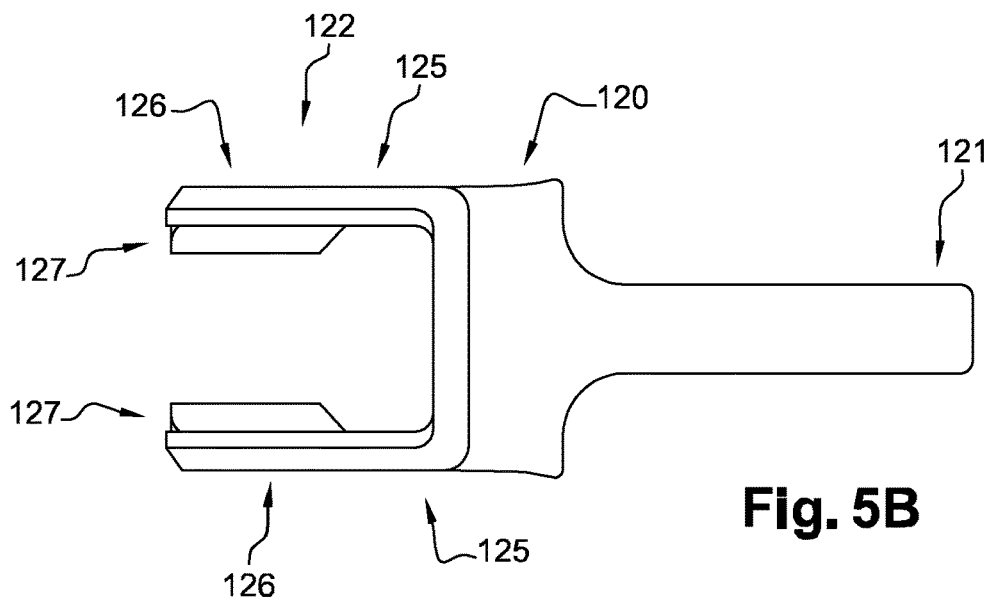
Figure 6:
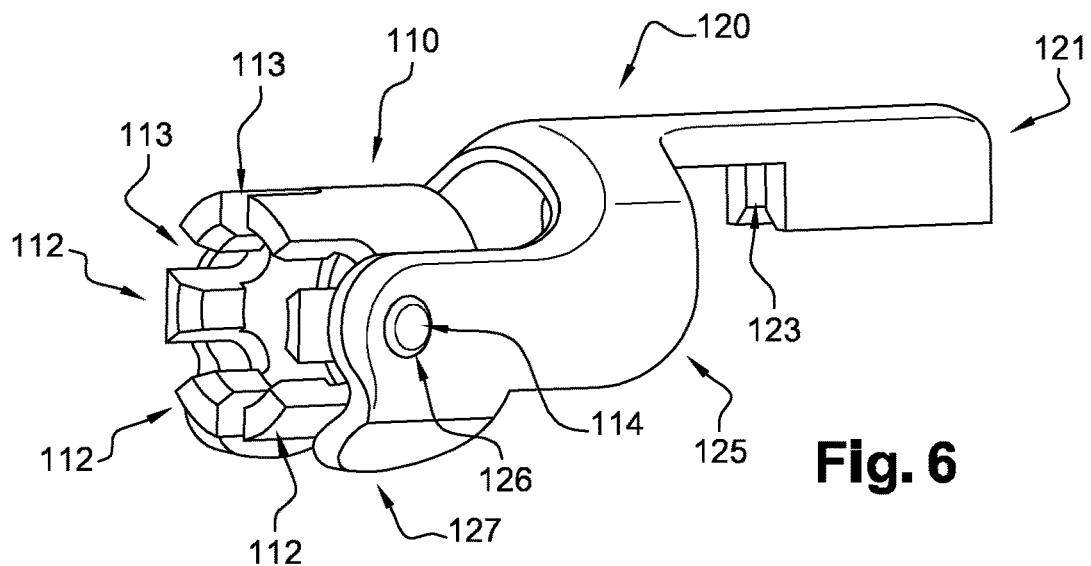
FIG. 6 is a perspective view of a mounting ring according to FIGS. 3A and 3B assembled with a shield according to FIGS. 5A and 5B.

FIGS. 5A and 5B disclose a shield 120 including a distal projection 121 and a proximal portion 122, the distal projection being provided with a notch 123 intended to accommodate at least the needle point 22 of a needle 20 and a hook 124 intended for locking onto the longitudinal tube 21 of the needle 20, when the shield 120 is mounted on the longitudinal tip of a syringe. The shield 120 is further provided in its proximal portion 122 with two proximal legs 125, each leg including a buckle 126 and a cam surface 127. The buckles 126 are intended to be assembled with the inserts 114 of the mounting ring 110 in a pivoting link as visible in FIG. 6, the mounting ring 110 being accommodated in the proximal portion 122 of the shield 120. The shield 120 may be made in the same material as the mounting ring 110. It can be either opaque or transparent.

The mounting ring 110 may thus allows a pivotal mounting of the shield 120 to the tip 14 of a syringe 10 when it is not possible to have inserts directly on the tip 14, for example when the syringe 10 is made of glass. However, plastic syringes or injectors may be manufactured with integrated inserts allowing a mounting pivotally the shield 120 directly to the tip 14 without the need of a mounting ring 110. Alternatively, the pivot link between the shield 120 and the mounting ring 110 or the tip 14 may be a plastic hinge i.e. a flexible plastic link allowing a rotative movement between the shield 120 and the mounting ring 110 or the tip 14.

Figure 7A:
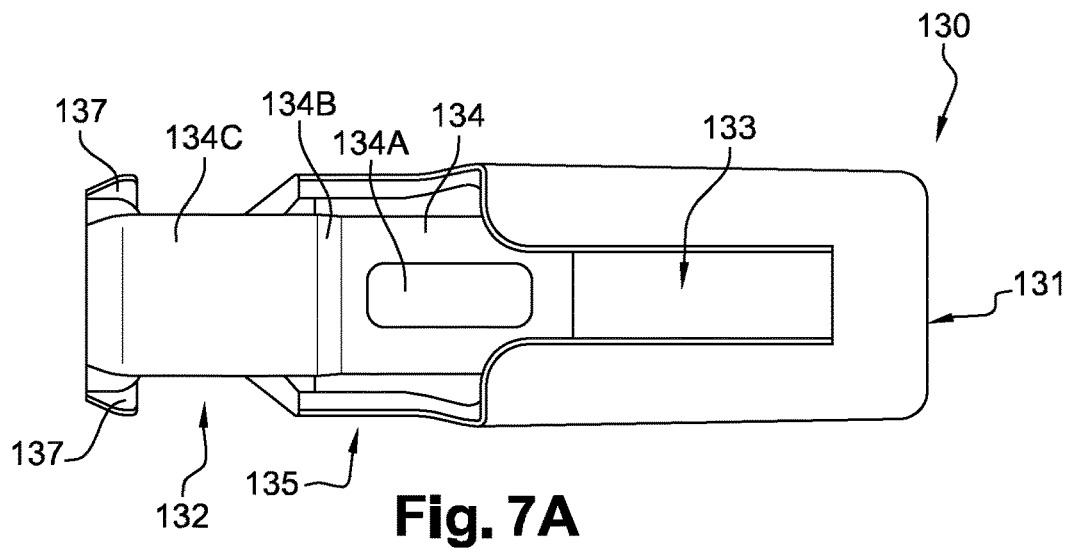
FIGS. 7A and 7B are a top view and a perspective view of a protective cap according to the present disclosure.
Figure 7B:
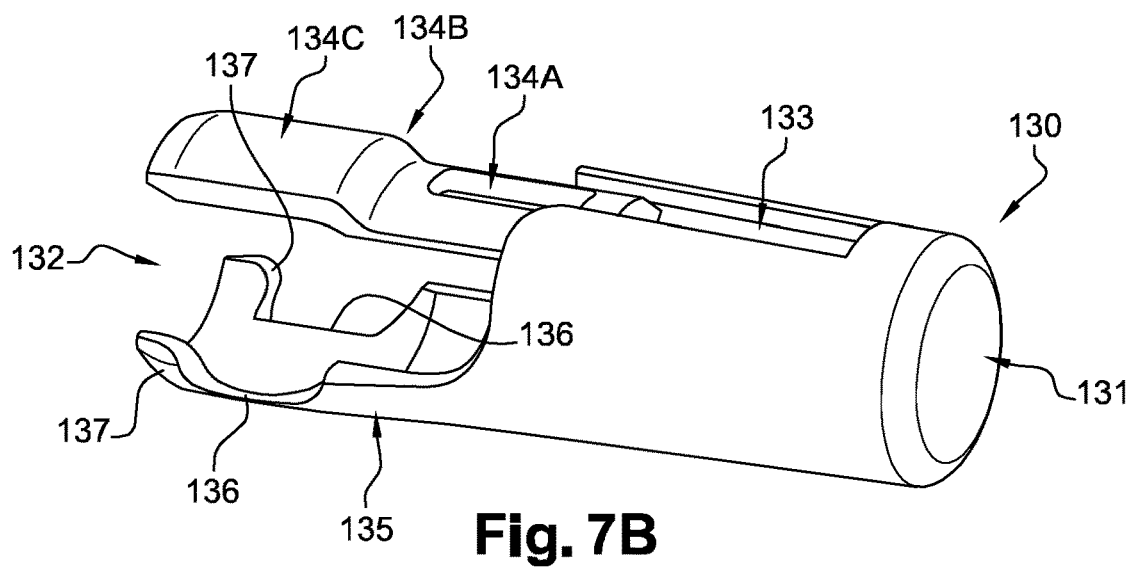

A protective cap 130 according to the present disclosure is visible in FIGS. 7A-7B. It includes a tubular body 131 with an inner cavity 132, a distal radial opening 133 and a top proximal extension 134 contiguous to the distal radial opening 133. The top proximal extension 134 is provided with a proximal radial opening 134A, a shoulder 134B and a proximal portion 134C. The top proximal extension 134 is substantially parallel to an opposite bottom proximal extension 135 provided with two curved cuts 136 and two engaging pegs 137. Both the top proximal extension 134 and the bottom proximal extension 135 show a curvature radius so as to respect the globally tubular shape of the body 131. The protective cap 130 may be made in the same material as the mounting ring 110. It can be either opaque or transparent.

Figure 8A:
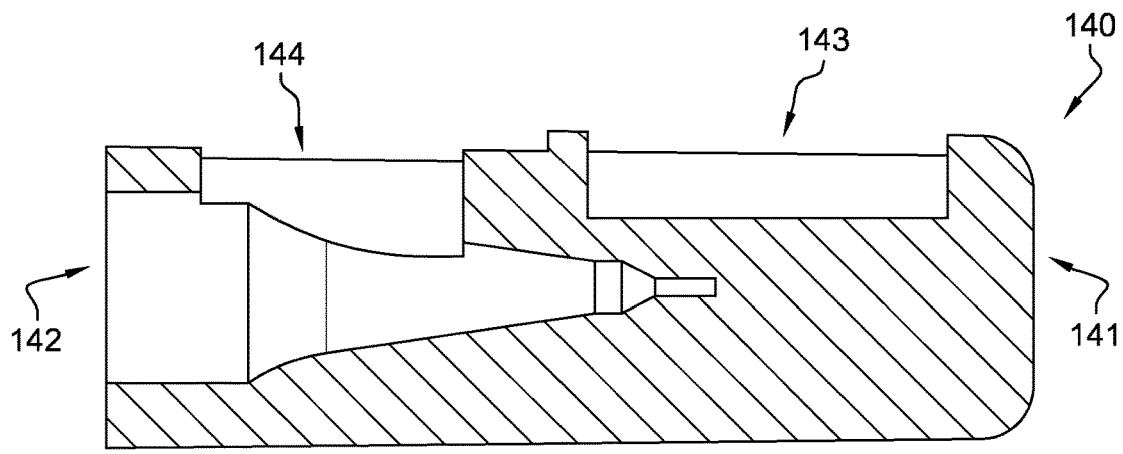
FIGS. 8A, 8B and 8C are respectively a cross-section view, a top view and a perspective view of a sealing cap according to the present disclosure.
Figure 8B:
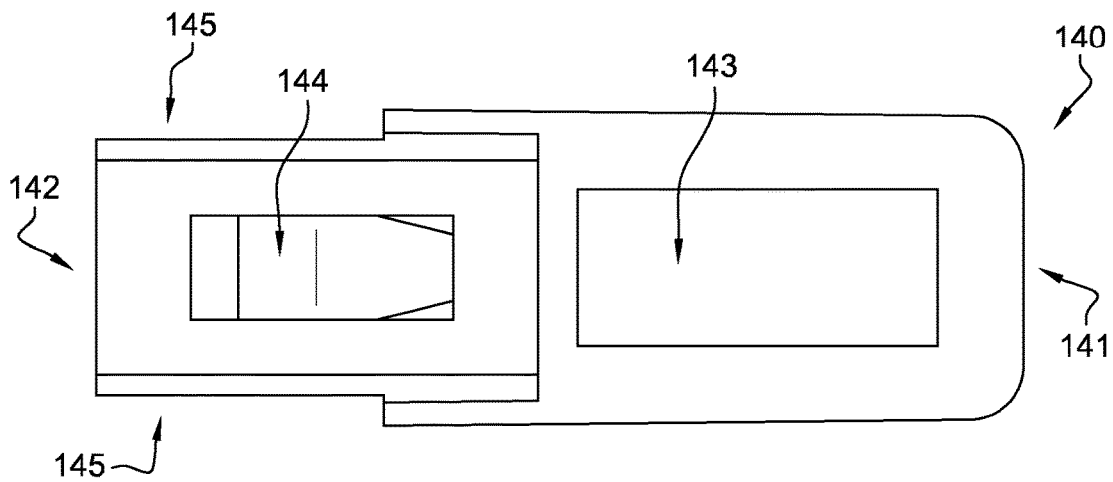
Figure 8C:
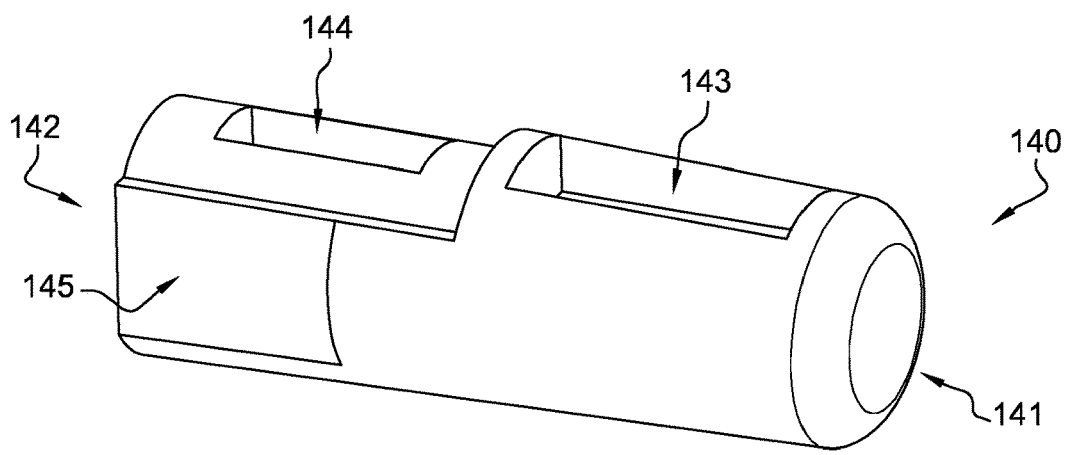

Now referring to FIGS. 8A-8C, an optional sealing cap 140 is described. This sealing cap 140 includes a cylindrical body 141 and an inner cavity 142. The inner cavity 142 has globally a conical shape and is intended to accommodate the longitudinal tip 14 and the needle 20 of the syringe 10. On its top portion, the sealing cap includes a distal radial recess 143 and a proximal radial opening 144, while it includes two opposite transversal surfaces 145 on its proximal portion.

Figure 9A:
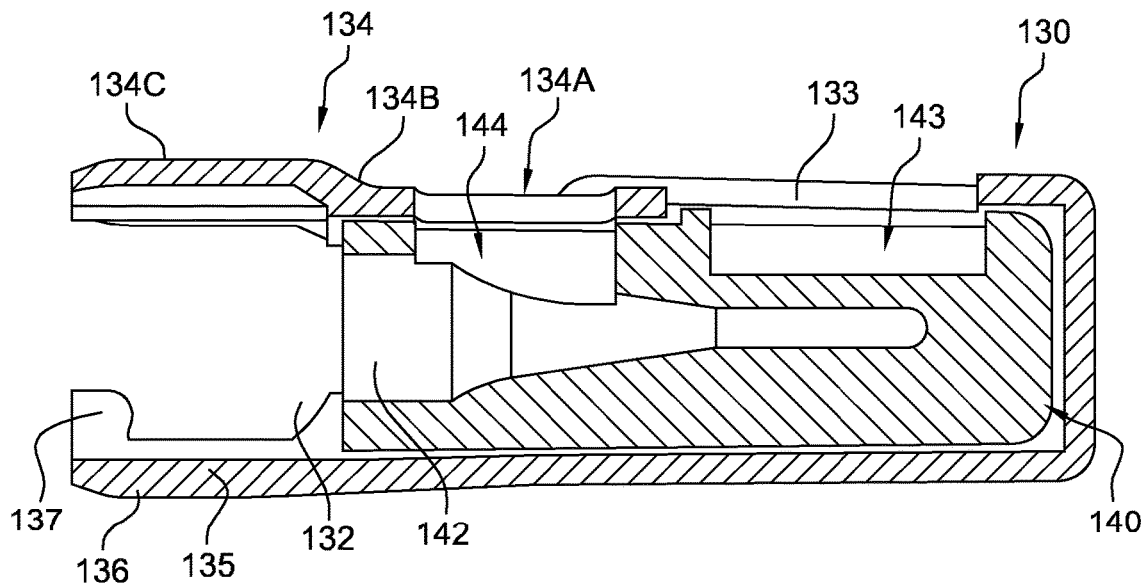
FIGS. 9A and 9B are respectively a cross-section view and a side view of a protective cap according to FIGS. 7A and 7B provided with a sealing cap according to FIGS. 8A-8C.
Figure 9B:
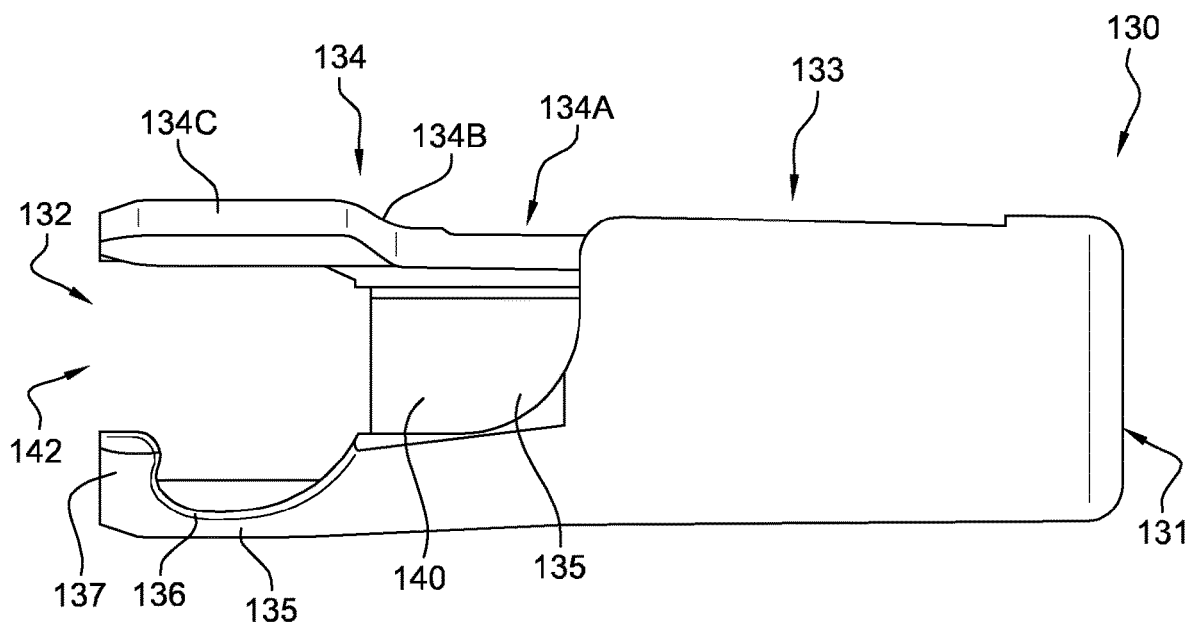

The sealing cap 140 is dimensioned to be accommodated inside the inner cavity 132 of the protective cap 130 (see FIGS. 9A and 9B). Once assembled the distal radial recess 143 of the sealing cap 140 faces and closes the distal radial opening 133 of the protective cap 130. Similarly, the proximal radial opening 144 of the sealing cap 140 faces the proximal radial opening 134A of the protective cap 130. The opposite proximal surfaces 145 and the internal surface of the distal radial recess 143 are the only portions of the sealing cap 140 visible when the sealing cap 140 is inserted into the protective cap 130.

The sealing cap 140 may be valuable to seal the needle point 22 of a prefilled syringe by pricking the needle point 22 into the material of the sealing cap 140, as visible in FIG. 12A. To this end, the material of the sealing cap may be a thermoset or thermoplastic elastomer such as poly(ethylene-propylene-diene) monomer (EPDM), poly(styrene-butadiene) rubber (SBR), isopropylene isobutylene rubber (IIR), polystyrene-b-poly(ethylene-butylene)-b-polystyrene (SEBS), polystyrene-b-polybutadiene-b-polystyrene (SBS), nitrile butadiene rubber (NBR), natural rubber (NR), isoprene rubber (IR) or butadiene rubber (BR) or combination thereof.

Figure 10A:
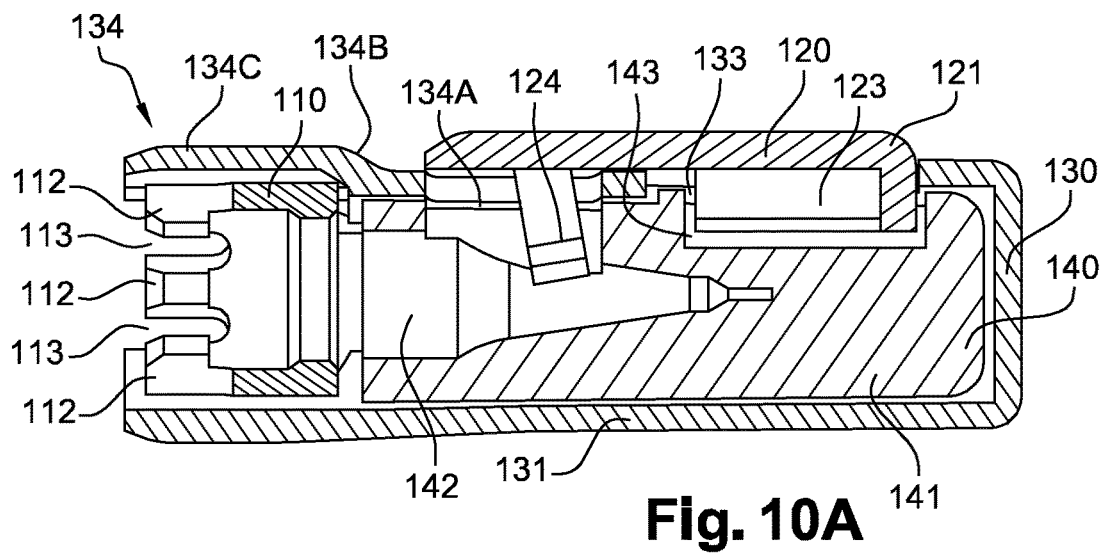
FIGS. 10A, 10B and 10C are respectively a cross-section view, a top view and a side view of an example of a safety device according to the present disclosure including the mounting ring of FIGS. 3A and 3B, the shield according to FIGS. 5A and 5B, the protective cap of FIGS. 7A and 7B and the sealing cap of FIGS. 8A-8C.
Figure 10B:
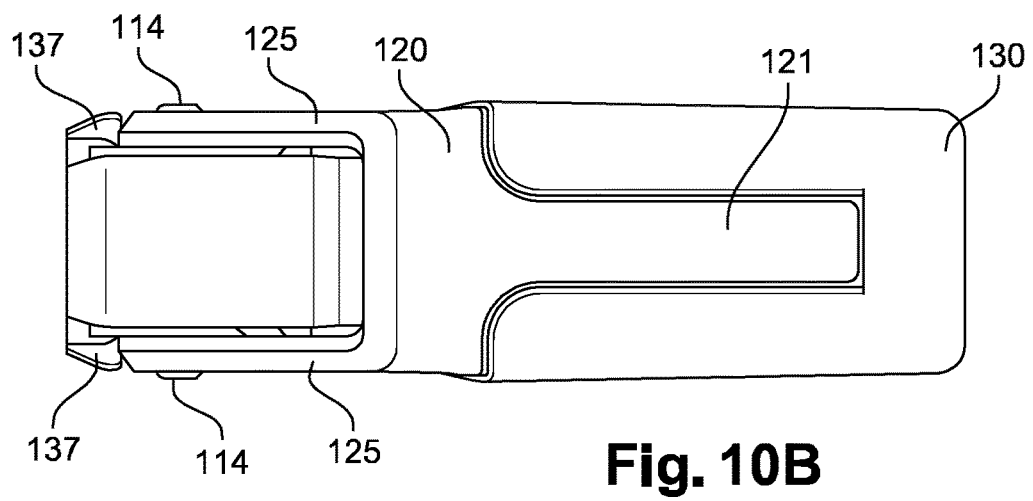
Figure 10C:
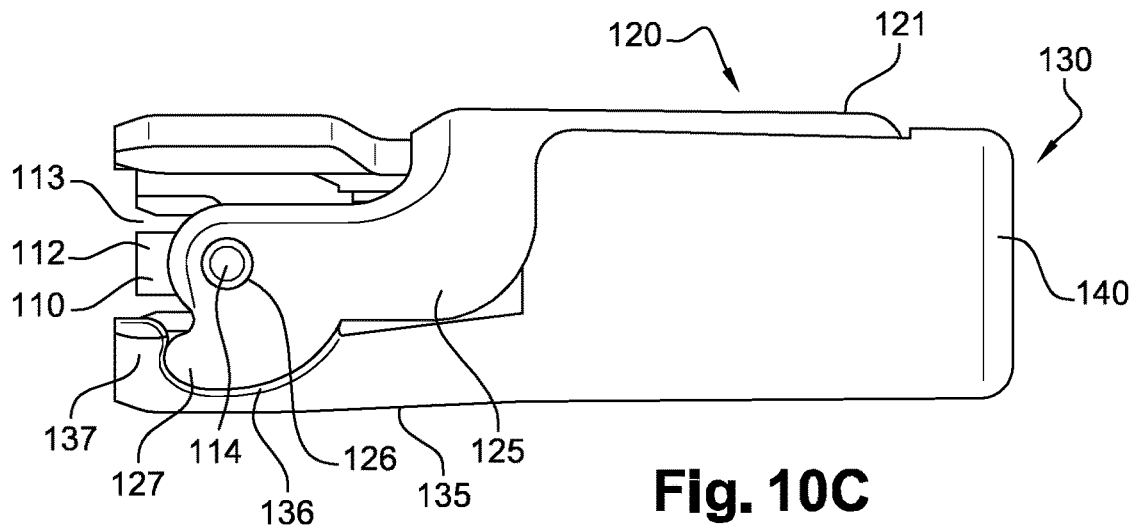

The protective cap 130 is designed to be complementary and interlocked with the shield 120 and the mounting ring 110, in a storage position as visible in FIGS. 10A-10C. The extension 121 of the shield 120 is totally accommodated between the distal radial opening 133, the shoulder 134B of the protective cap 130, the notch 123 of the shield 120 being accommodated in the distal radial opening 133 of the protective cap 130. In addition, the hook 124 of the shield 120 is accommodated into the proximal radial opening 134A of the protective cap 130 and the top and bottom proximal extensions 134, 135 overlap the mounting ring 110 that is pivotally connected to the shield 120. Furthermore, the shield 120 and the protective cap 130 are dimensioned and interlocked such that the two curved cuts 136 of the protective cap 130 accommodate the cam surfaces 127 while the two engaging pegs 137 of the protective cap 130 engage the cam surfaces 127 of the shield 120, as visible in FIG. 10C.

The protective cap 130, the shield 120, optionally the mounting ring 110 and the sealing cap 140 are thus totally interlocked in an example of a safety device 100 according to the present disclosure. Such a safety device 100 can be provided as a pre-assembled sub-unit for a straightforward mounting on the longitudinal tip 14 of a syringe 10. The mounting step may be done by a single-step by application of a fitting transversal force for arrangement of the safety device 100 onto the longitudinal tip 14 of the syringe 10.

The operating process for using a safety device 100 will now be described with reference to FIGS. 11A to 11F and 12A to 12F. A syringe 10 is presented with a safety device 100 to the medical staff according to FIGS. 11A and 12A: the safety device 100 is mounted onto the longitudinal tip 14 of the syringe 10, the shield 120 is in the storage position, interlocked with the protective cap 130 and substantially parallel to the needle 20, which is enclosed by the protective cap 130. Furthermore, the needle point 22 is embedded in the elastomeric material of the elastomeric inner cap 140 avoiding any leakage of the contents of the reservoir 12 of the syringe 10, which is valuable when the syringe 10 has been prefilled with a medical product. The protective cap 130 is useful to protect the needle 20 prior use, for example from shocks, dusts and contact with any contaminations. The elastomeric inner cap 140 maintains the sterility and the sealing of the needle 20.

In a first step, the medical staff may open the safety device 100 by pinching and drawing the protective cap 130 in the distal direction. As soon as the protective cap 130 moves distally, the engaging pegs 137 of the protective cap 130 push onto the cam surfaces 127 of the shield 120, which results into a rotary, opening movement of the shield 120 towards the syringe barrel 11 as visible in FIGS. 11B and 12B. The rotary movement of the cam surfaces 127 is optimized by the specific shapes of the curved cuts 136 which allow a smooth and natural movement, similar to the opening of a needle cap that does not have any safety devices. Because of this rotary movement, the hook 124 and the notch 123 of the shield 120 escapes respectively from the proximal radial opening 134A and the distal radial opening 133 of the protective cap 130.

In FIGS. 11C and 12C, the opening of the protective cap 130 by distal translation is almost completed, the engaging pegs 137 being barely disengaged from the cam surfaces 127 and the needle 20 becoming visible.

Figure 11D:
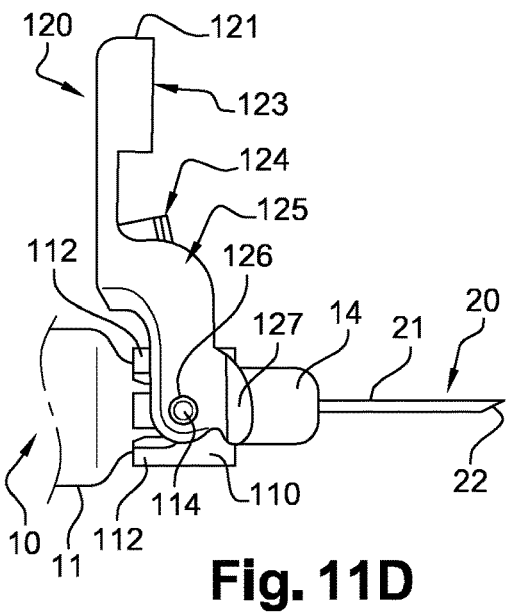
Figure 12D:
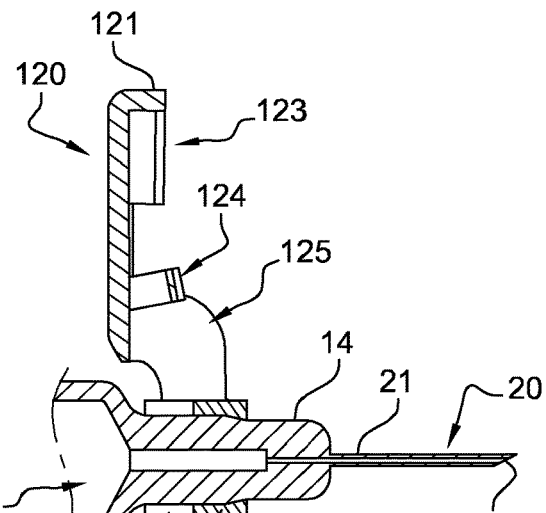

In FIGS. 11D and 12D, the safety device 100 is fully open since the protective cap 130 has been removed and the shield 120 has rotated into a retracted position. Thanks to the proximal position of the cam surfaces 127 and the engaging pegs 137 as regards as the pivot link made by the buckles 126 and the insert 114, the shield 120 is doing substantially a right angle with the needle 20 after rotation and is giving full access to this needle 20. The syringe 10 is now ready to be used, for example to inject a medical product into the body of a patient. Furthermore, the shield 120 in the retracted position does not prevent a direct view on the needle 20 and especially the needle point 22 which allows an injection in safe and comfortable conditions, both for patients and medical staff.

Figure 11E:
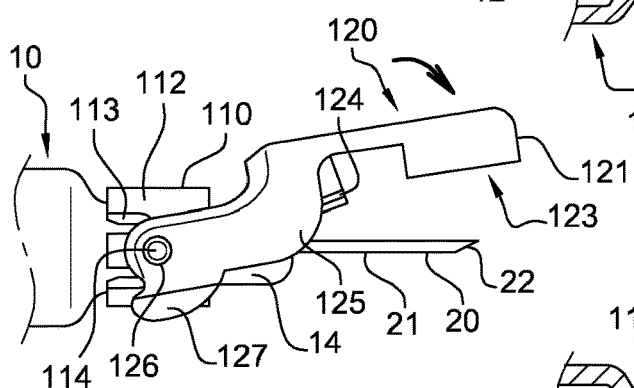
Figure 12E:
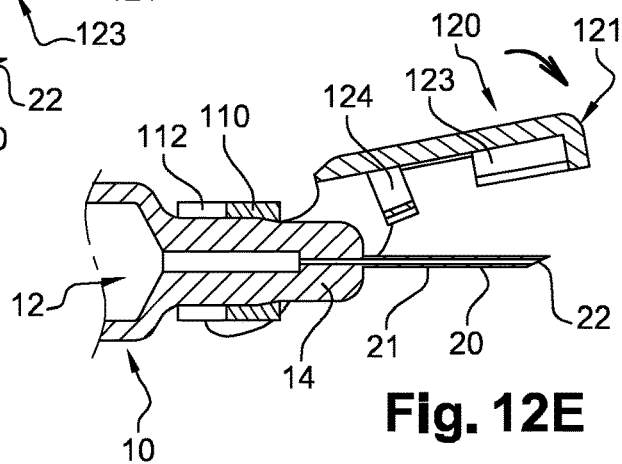

Once the injection is performed, the shield 120 may be moved to a safety position where it covers the needle 20 by applying a force with a thumb or a surface (see FIGS. 11E and 12E). The force yields to a rotation of the shield 120 toward the needle 20, because of the pivoting link realized by the inserts 114 and the buckles 126. This operation is safe for the medical staff as the thumb is protected by the shield from needle stick injury.

Figure 11F:
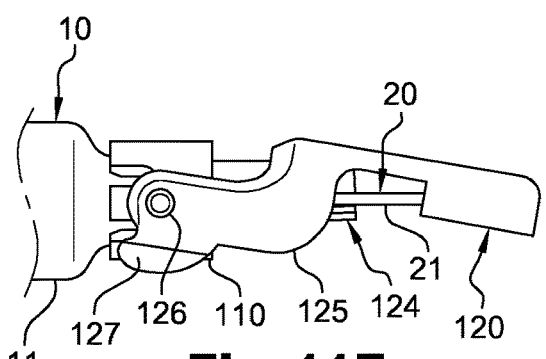
Figure 12F:
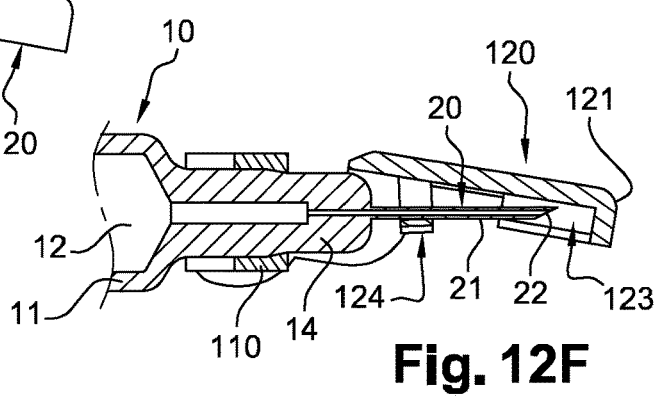

At the end of the rotating movement, the shield 120 covers the needle 20, is further locked on the needle longitudinal tube 21 by the hook 124 and the needle point 22 is accommodated into the notch 123, as visible in FIGS. 11F and 12F. In this position, the needle point 22 is hidden by the notch 123 (see FIG. 12F) and the shield 123 prevents any needle stick injury.

As applicable, all individual features that are shown in the individual embodiments can be combined and/or exchanged with each other without departing from the scope of the disclosure.

The invention claimed is:

1. A safety device for preventing needle stick injury with a needle of a medical device, the needle comprising a proximal end fixed to a tip of the medical device and a distal end provided with a needle point, the safety device comprising:
    a protective cap mounted on the tip of the medical device to at least cover the needle point, the protective cap comprising a proximal extremity provided with an engaging peg, and
    a shield mounted by a pivot link around the tip of the medical device such that the shield adopts a storage position where the shield is interlocked with the protective cap, a retracted position where the shield gives access to the needle and a safety position where the shield covers the needle, the shield comprising a cam surface at a proximal extremity,
    wherein the cam surface and the engaging peg are located proximally from the pivot link and arranged so that, when the safety device is mounted around the tip of the medical device, removing the protective cap from the tip by a distal movement displaces the shield from the storage position to the retracted position.

2. The safety device according to claim 1, wherein the shield is provided with two cam surfaces and the protective cap is provided with two engaging pegs.

3. The safety device according to claim 1, wherein the shield is provided with two proximal legs, each leg comprising a buckle, the safety device further comprising a mounting ring adapted to be mounted onto the tip of the medical device and provided with two opposing inserts adapted to be assembled with the buckles of the shield in a pivoting link so as to pivotally mount the shield to the tip when said mounting ring is mounted to the tip.

4. The safety device according to claim 1, wherein the shield is further provided with a hook such that, when the safety device is mounted on the tip of the medical device and the shield is in the safety position, said hook irreversibly locks said shield onto the needle.

5. The safety device according to claim 4, wherein the protective cap comprises a proximal radial opening positioned and dimensioned to accommodate the hook of the shield when the shield is in the storage position.

6. The safety device according to claim 1, wherein the shield is further provided with a notch, so that, when the safety device is mounted on the tip of the medical device and the shield is in the safety position, the notch hides the needle point.

7. The safety device according to claim 6, wherein the protective cap further comprises a distal radial opening positioned and dimensioned to accommodate the notch of the shield when the shield is in the storage position.

8. The safety device according to claim 1, wherein said safety device is further provided with a sealing cap accommodated in the protective cap to seal the needle point.

9. A medical device having a tip provided with a needle comprising a proximal end fixed to the tip of the medical device and a distal end provided with a needle point the medical device further comprising a safety device according to claim 1.

* * * * *